United States Patent [19]

Eisert

[11] 4,352,558
[45] Oct. 5, 1982

[54] APPARATUS FOR MEASURING PARTICLE CHARACTERISTICS

[75] Inventor: Wolfgang Eisert, Hanover, Fed. Rep. of Germany

[73] Assignee: Gesellschaft fur Strahlen-und Umweltforschung mbh, München, Neuherberg, Fed. Rep. of Germany

[21] Appl. No.: 200,378

[22] Filed: Oct. 24, 1980

[30] Foreign Application Priority Data

Oct. 25, 1979 [DE] Fed. Rep. of Germany ....... 2943116

[51] Int. Cl.$^3$ ...................... G01N 33/48; G01N 21/64
[52] U.S. Cl. ........................................ 356/39; 356/73; 356/336; 356/440; 422/81; 250/461.2
[58] Field of Search ................... 356/39, 73, 335, 336, 356/440, 442; 250/461 B, 222 PC; 422/81

[56] References Cited

U.S. PATENT DOCUMENTS 4,110,043 8/1978 Eisert ................................. 356/336

FOREIGN PATENT DOCUMENTS 2543310 3/1977 Fed. Rep. of Germany .

OTHER PUBLICATIONS

"Quantitative Aspects of Rapid Microfluorometry for the Study of Enzyme Reactions and Transport Mechanisms in Single Livine Cells", Kohen et al., pp. 207-217 in the text Fluorescence Techniques in Cell Biology, published by Springer Verlag, 1973, Heidelbery-New York.

*Primary Examiner*—Vincent P. McGraw
*Attorney, Agent, or Firm*—Spencer & Kaye

[57] ABSTRACT

In apparatus for measuring reaction and/or diffusion of particles suspended in a fluid, which apparatus includes a supply tube for supplying a stream of the particle-containing fluid, a tapered tube surrounding the supply tube for providing a first entraining fluid stream and for encasing the particle-containing fluid in the first entraining fluid stream for the purpose of hydrodynamically focusing the particle-containing stream into a thin stream enclosed by the first fluid and in which the particles are separated from one another, an outlet for passage of the thin stream and first fluid stream after leaving the tube, a device producing a radiation beam which intersects the thin particle-containing stream, a detector disposed for detecting the radiation emanating from the separated particles, and a pulse evaluation circuit connected to the detector, there is provided a further tube surrounding the supply tube and forming a further entraining fluid stream concentric with the particle-containing stream and the first entraining fluid stream, surrounding the particle-containing stream and flowing therewith through the tapered tube, the further entraining fluid stream having a composition selected to interact with the particles.

4 Claims, 6 Drawing Figures

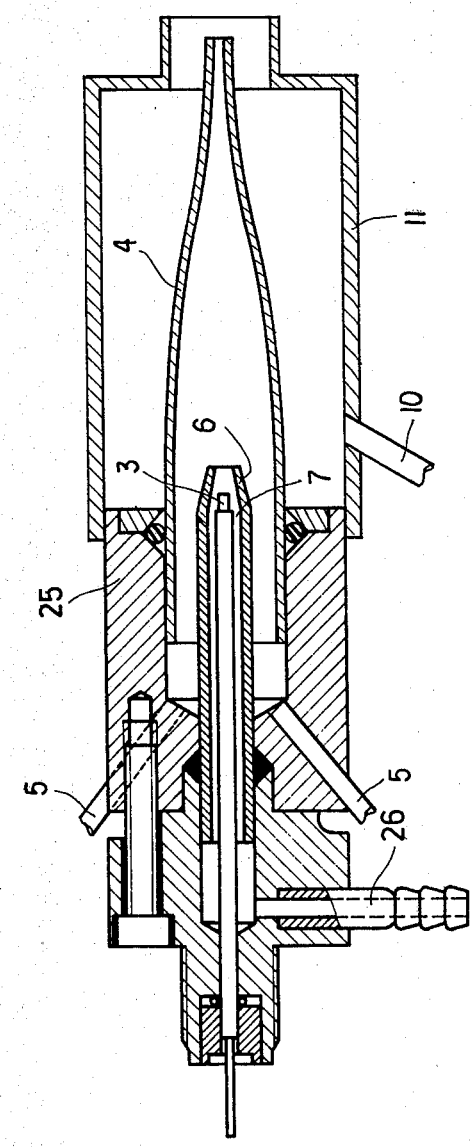

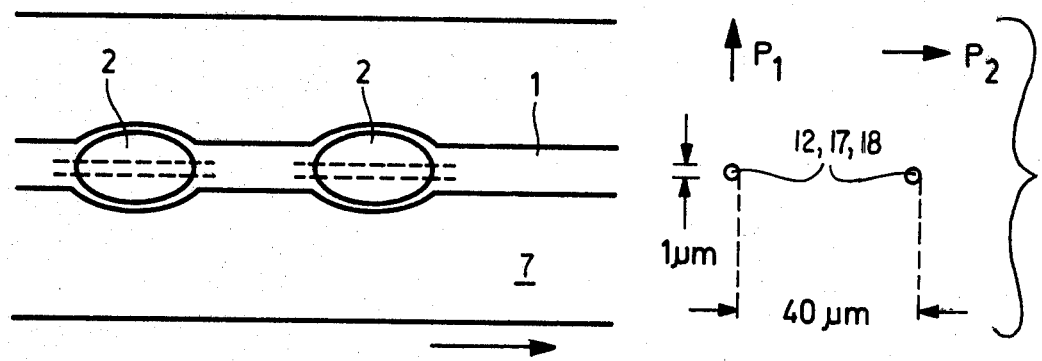
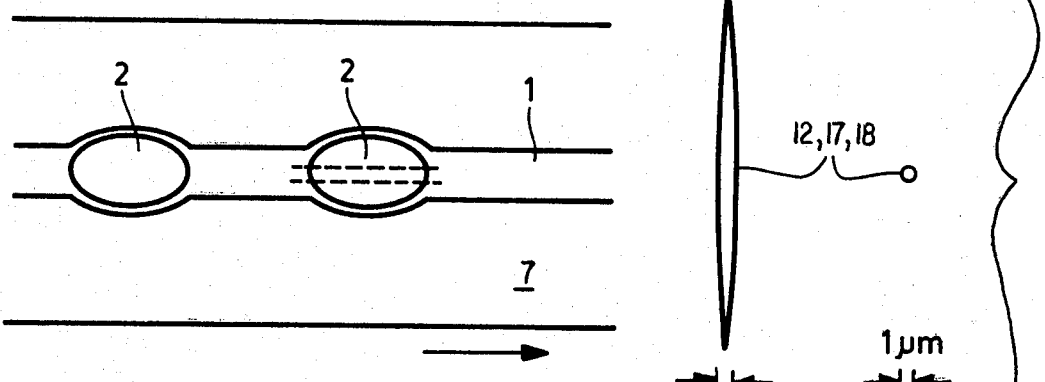
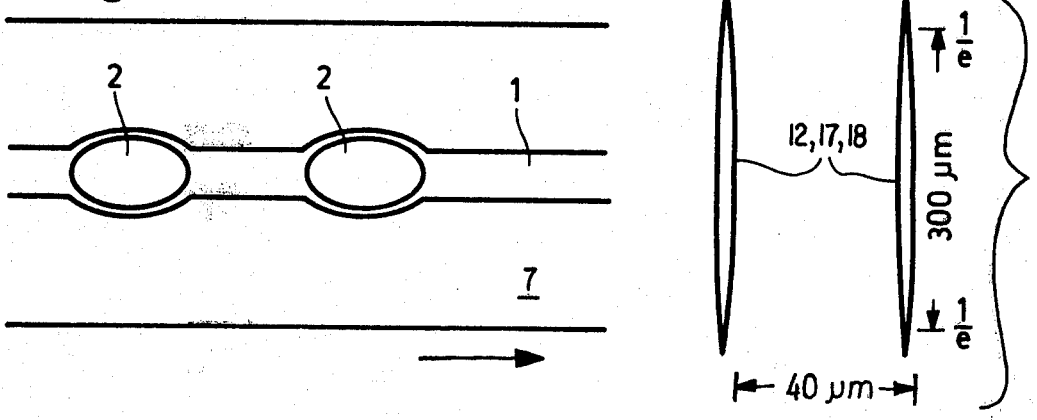

APPARATUS FOR MEASURING PARTICLE CHARACTERISTICS

BACKGROUND OF THE INVENTION

The present invention relates to an apparatus for measuring reactions and/or diffusion experienced by particles suspended in a fluid for the purpose of measuring cells.

Known cell measuring apparatus includes a tapered pipe through which flows the suspension and a first entraining fluid for hydrodynamically focusing the suspension into a thin stream of suspension in which the particles are arranged in a single file and which, after leaving the pipe, is brought to an outlet together with the first entraining fluid. Such apparatus further includes an illumination and/or observation beam which intersects the thin stream of suspension, and at least one detector connected to a pulse evaluation circuit for detecting the radiation emanating from the individual particles.

Apparatus of this type is disclosed in my German Offenlegungsschrift [Laid-open Application] No. 2,543,310 and counterpart U.S. Pat. No. 4,110,043. However, this device is capable only, inter alia, of counting and classifying individual particles. It cannot be used to measure the movement of substances into and out of the particles, which may be cells, or chemical reactions at the particles because, on the one hand, the reaction fluid causes the illuminating and/or observation beam to be absorbed and, on the other hand, a minimum diameter would have to be maintained for the first entraining fluid to assure stabilization of the hydrodynamic focus. Therefore in this prior art apparatus this entraining fluid cannot be used as the reaction fluid.

In the past, such measurements were successful only when performed on individual particles with direct microscopic observation, as described by Elli Kohen et al in the section "Quantitative Aspects of Rapid Microfluorometry for the Study of Enzyme Reactions and Transport Mechanisms in Single Living Cells," of the text *Fluorescence Techniques in Cell Biology*, published by Springer Verlag, 1973, Heidelberg-New York, 5, at pages 207-17. This method employed dye reactions, radioactive or immunological techniques.

Such techniques or measurements can be employed only with individual particles which are not necessarily representative of the total quantity of particles or, if measurements are made with particles in suspension, do not permit any detailed information to be obtained about the individual particles.

SUMMARY OF THE INVENTION

It is therefore an object of the present invention to enable such measurements to be made while also making it possible to first obtain a reaction product from the two entraining fluids, which product then interacts with the particles.

This and other objects are achieved, according to the invention, in apparatus for measuring reaction and/or diffusion of particles suspended in a fluid, which apparatus includes a supply tube for supplying a stream of the particle-containing fluid, a tapered tube surrounding the supply tube for providing a first entraining fluid stream and for encasing the particle-containing fluid in the first entraining fluid stream for the purpose of hydrodynamically focusing the particle-containing stream into a thin stream enclosed by the first fluid, means defining an outlet for passage of the thin stream and first fluid stream after leaving the tube, means producing a radiation beam which intersects the thin particle-containing stream detector means disposed for detecting the radiation emanating from the separated particles, and a pulse evaluation circuit connected to the detector, by the provision of a further tube surrounding the supply tube and forming a further entraining fluid stream concentric with the particle-containing stream and the first entraining fluid stream, surrounding the particle-containing stream and flowing therewith through the tapered tube, the further entraining fluid stream having a composition selected to interact with the particles.

The present invention thus permits the capabilities of highly resolving flow cytometry to be expanded by provision of the further entraining fluid stream which contains the reaction solution. This makes it possible to measure individual cells and particles in rapid succession while simultaneously permitting other parameters of each cell to be detected. Microscopic resolution is here retained even at high measuring rates. After leaving the sample supply tube, the suspension is entrained by a concentric fluid or reaction stream, respectively, which contains reaction or dye substances. Both are hydrodynamically focused in a known manner and an auxiliary entraining stream permits, in special cases, optical adaptation to planar observation windows.

The diameter ratio of the suspension stream to the reaction fluid stream can be selected on the basis of the desired test conditions. If, for example, the reaction solution exhibits a high inherent absorption, the final diameter of the reaction solution stream will be made only slightly larger than the cells. With insignificant losses in accuracy of the spatial positioning for hydrodynamic focusing, different reaction periods can be set upstream of the measuring point by displacing the opening of the suspension supply pipe along the flow axis or by varying the flow velocity. The selection of the substance concentration in the reaction solution pipe permits the setting of different diffusion gradients. With fluorochromated substances, the magnitude of the scanning beam is limited only by the spatial separation of the individual cells, i.e., it may be smaller as well as larger than the cell diameter.

However, the system makes it possible for the first time to perform diffusions and reactions with individual cells and particles in suspensions with adjustable reaction periods and/or diffusion gradients at a high measuring rate. In addition to reaction data, other parameters of the cells and particles can be determined and used for attaining a more precise characterization of the cells. Moreover, highly resolving examinations are possible with systems in diffusion equilibrium as well as before they reach the equilibrium state. The measurement of individual particles in large numbers provides information with high statistical reliability.

BRIEF DESCRIPTION OF THE DRAWING

FIG. 2 is a cross-sectional detail view of a preferred embodiment of a fluid stream forming component of the apparatus of FIG. 1.

FIGS. 3a to 3c are cross-sectional detail views of a portion of a fluid stream formed according to the invention.

DESCRIPTION OF THE PREFERRED EMBODIMENTS

Figure 1:
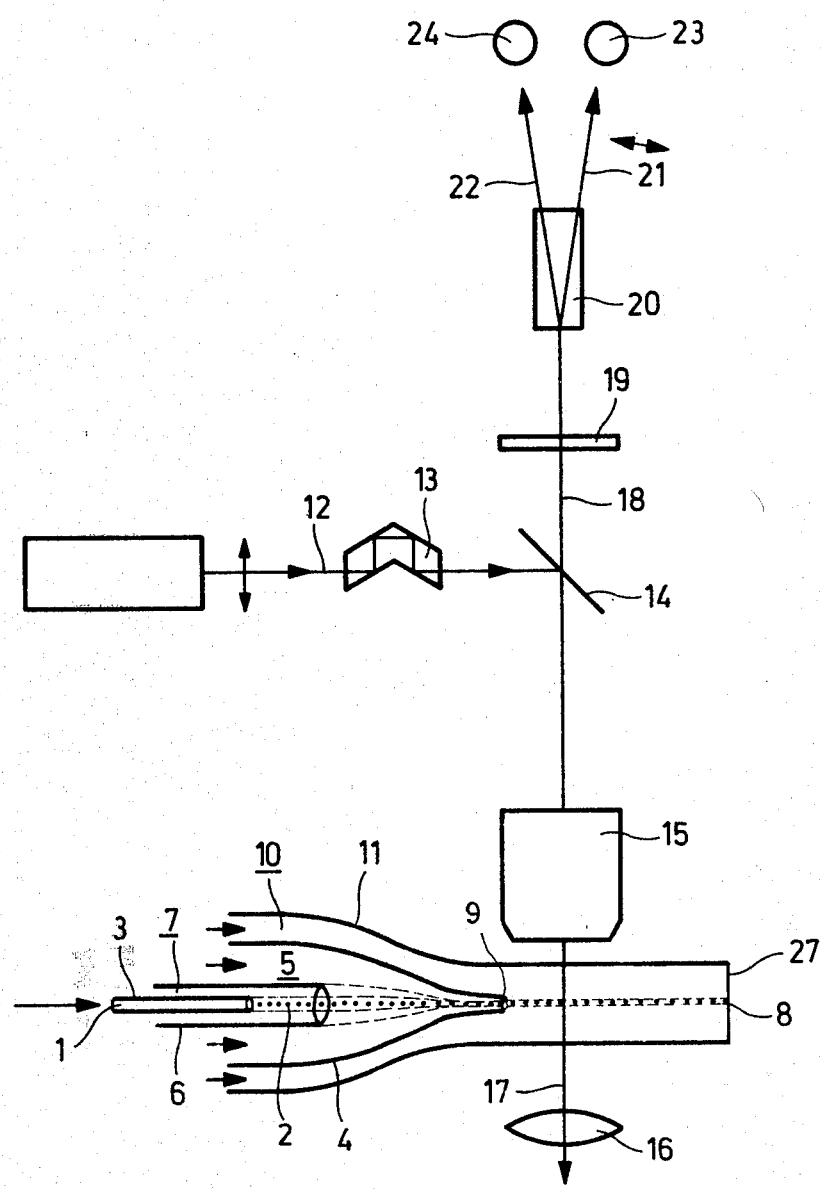
FIG. 1 is a simplified pictorial view of a preferred embodiment of a cell property measuring apparatus according to the invention.

FIG. 1 is a schematic representation of an apparatus according to the invention including illuminating and measuring components. A sample suspension 1 composed of particles 2 in a suspension fluid flows through an inlet pipe, or tube, 3 into a tapering tube 4 to be hydrodynamically focused. A first entraining fluid stream 5 is introduced through tube 4 so as to form a thin stream of suspension, in a manner similar to that effected in the apparatus disclosed in the above-cited prior art.

Around the inlet tube 3 concentric with tubes 3 and 4, there is disposed a further tube 6 through which a reaction fluid 7 is introduced to form a further entraining fluid stream. The particles 2, the suspension fluid 1 and the reaction fluid 7 are then focused in stream 5 by passage through the outer, tapered tube 4 as shown, for example, in FIGS. 3a–c.

In the apparatus shown in FIG. 1, tube 3 is to be movable in the direction of flow relative to the further tube 6 and both tubes 3 and 6 are to be movable in the flow direction relative to the outer tube 4. By means of these displacements, it is possible to vary the diameter of the thin stream of suspension 1 as well as that of the reaction fluid 7.

The jointly formed stream of fluid 8 then leaves the nozzle end 9 of the outer tube 4 either in free flight, in which case stream 8 is directed vertically downwardly, or entrained in an auxiliary entraining fluid stream 10 until it reaches outlet 27, the further entraining fluid being introduced through a jacket pipe 11 surrounding and projecting downstream beyond tube 4. This further fluid may serve, for example, to stabilize the fluid stream 8 or to achieve optical adaptation. It may, however, also be eliminated if only stray or fluorescent light emanating from the particles 2 is to be observed.

Illumination, observation and evaluation are effected by use of a laser beam 12 which is directed onto the particles 2, or the common stream of fluid 8, respectively, via a polarization rotator 13, which is not indispensable, a dichroic mirror 14, providing Epi illumination, and an optical objective 15. Epi illimination is that used to effect backward fluorescence and scattering detection.

Observation, or measurement, is performed on transmitted light beam 17 as well as light which is scattered forward over a narrow angle from the particle stream, passing through a lens 16, or on stray or reflected light or fluorescent emissions 18, passing through interference filter 19 and calcite crystal 20 to form polarized partial beams 21 and 22 which are received by photomultipliers 23 and 24, respectively. The two beams 21 and 22 serve, for example, to permit measurement of emission anisotropy. Suitable commercially available calcite crystal devices are commonly known as Wollaston prisms. A device typically having an aperture size of 10 mm × 10 mm could be employed in the apparatus of FIG. 1.

The pulse evaluation circuit is not shown since it is essentially similar to the circuit disclosed in the above-cited prior art. Instead of being separated according to different directions of polarization, the observation beam can also be split with the aid of prisms or semi-transparent mirrors into several different wavelength ranges.

FIG. 2 is a detail view of one embodiment of a device for forming the fluid streams. The supply tube 3 and the tube 6 are fastened in a metal chamber 25 that is open at one end. Tube 3 is enclosed in a sheath provided to support and rigidify the tube. The axial displaceability of the two pipes 3 and 6 with respect to one another and with respect to the outer pipe 4 (see FIG. 1) is not shown in detail. However, it can be effected by known displacement techniques. The reaction fluid 7 is introduced through a nipple 26 disposed at the side of housing 25.

FIG. 2 also shows the mounting of a tube 4 and jacket pipe 11 on housing 25. According to one advantageous feature, tube 4 is formed to converge according to a calculated hyperbolic pattern in such a manner as to assure that the fluid flow velocity in that portion of the tube will increase in a linear manner parallel to the flow axis. This will have the effect of reducing stress, in the axial direction, on cells or particles being monitored and will thus help to assure that the particles remain intact and experience a minimum of stretching in the axial direction. As a result, more reliable and accurate cell length measurements can be assured. In practical embodiments of the invention, it has proven possible to limit axial cell elongation to values of 2% even for very flexible cells such as red blood cells.

FIG. 2 further illustrates fluid inlets to tube 4 and pipe 11. Advantageously, these inlets can be oriented so that their axes are skewed relative to, or pass to one side of, the flow axis, to thereby impart a stabilizing vortex component to the fluid entering tube 4 and pipe 10.

FIGS. 3a–3c each show two particles 2 which are aligned in a single file row along the thin stream of suspension 1. In the illustrated embodiment, the suspension fluid 1 encloses the particles 2 in the form of a thin film. Particles 2 and suspension 1 move in the direction of the horizontal arrow together with the reaction fluid 7.

To the sides of FIGS. 3a–3c, two small arrows $P_1$ and $P_2$ are shown which indicate two of the possible directions of polarization of the two parallel excitation beams, and there are shown the cross sections of two parallel illumination or observation beams 12, 17 or 18.

The two beams shown in FIGS. 3a–3c could be produced simply by modifying the apparatus of FIG. 1 to include, in the path of beam 12 between rotator 13 and mirror 14, a beam splitter of a type which divides beam 12 into two laterally offset, substantially parallel beams which are then both reflected by mirror 14 and remain sufficiently close together to both be suitably focused by objective 15.

If the beams have circular radiation cross sections, as shown in FIG. 3a, it is possible to determine either the length of a cell, in which case the second beam 18 serves to correct the absolute values or, if excitation with the two beams takes place with two directions of polarization, for example, the mobility of fluorochromes.

Using one slit-shaped beam cross section and one circular beam cross section, as shown in FIG. 3b, it is possible to determine the length and width of particles 2. Particle length may be determined by measuring the time required for the particle to traverse the small diameter beam of circular cross section. Width is measured in the direction of the long dimension of the slit-shaped beam cross section by monitoring the intensity, across the entire beam cross section, of laser radiation emerging from the measuring region when radiation incident on the particle is extinguished, i.e. absorbed or deflected. Since the proportion of the beam intercepted by a particle depends on its width, the change in intensity of the radiation transmitted through the measuring zone during passage of a particle will be proportional to particle width. A reference value for the readings proportional to particle width could be the amplitude of the pulse produced in the circular beam of small diameter when traversed by a particle.

Two slit-shaped beam cross sections, as shown in FIG. 3c, permit the determination of cell lengths, in which case the particles are not necessarily perfectly aligned or have formed clumps. One beam then determines the length, as defined in the above-mentioned prior art, relative to the flow rate. Observation of the time of passage from the first beam to the second beam permits the flow rate itself to be determined. This makes it possible to calibrate the electronic evaluation system so as to display the absolute values of magnitude.

The parallel broken line pairs in FIGS. 3a and 3b depict the region covered by each beam 18 of circular cross section as a cell 2 traverses the beam.

According to one exemplary embodiment of the invention, the flow system shown in FIG. 1 could have the following dimensions:
Outlet diameter of tube 3 = 0.4 mm,
Outlet diameter of tube 6 = 2.0 mm,
Inlet diameter of tube 4 = 15–35 mm,
Diameter of nozzle end 9 = 0.2–0.3 mm,
Diameter of pipe 11 beyond nozzle 9 = 1.5 mm.

Corresponding axial dimensions would be selected on the basis of desired flow rates. By way of example, the axial distance between the outlet ends of tubes 3 and 6 could be of the order of 3–5 mm, that between the outlet end of tube 6 and nozzle 9 could be 70–80 mm, and that between nozzle 9 and the axis of beam 17 could be of the order of 1 mm.

Apparatus according to the invention could advantageously be utilized for examining the properties of a wide variety of particles, both organic and inorganic, as well as biological cells. By way of example, the apparatus could be used to measure the size, concentration and/or various optical characteristics of asbestos fibers or plastic microspheres suspended in a carrier liquid, such as water or oil, selected to not absorb the selected measuring radiation. The apparatus could similarly be employed to examine liquid droplets suspended in an immiscible liquid carrier.

As an example of the application of the invention to the study of biological cells, the apparatus could be employed for examining the response of biological cells to fluorescein or fluorescein diacetate. According to one such procedure, biological cells suspended in an esterase solution could be delivered through tube 3, while fluorescein diacetate in a carrier such as water or a saline solution constitutes fluid 7 delivered via tube 6. Between the outlet of tube 3 and nozzle end 9, the esterase reacts with the fluorescein diacetate to yield fluorescein which diffuses into cells 2. The concentration of fluorescein in each cell 2 at the time it traverses beam 18 can then be detected by the fluorescence generated by the beam.

According to a variant of this procedure, fluid 1 could be a saline solution, in which case the fluorescein diacetate in fluid 7 would diffuse into the biological cells 2 beyond the outlet of tube 3 and there react with esterase already present as a cell constituent.

In either case, the resulting fluorescence level is determined by the concentration of fluorescein in the cell, which is indicative of the cell pathology.

In the performance of examinations in apparatus according to the invention, entraining fluids 5 and 10 can typically be the same as the carrier of fluid 7. More generally, it is desired that fluids 1, 7, 5 and 10 be selected to have refractive indices which are as close as possible to one another.

Figure 4:
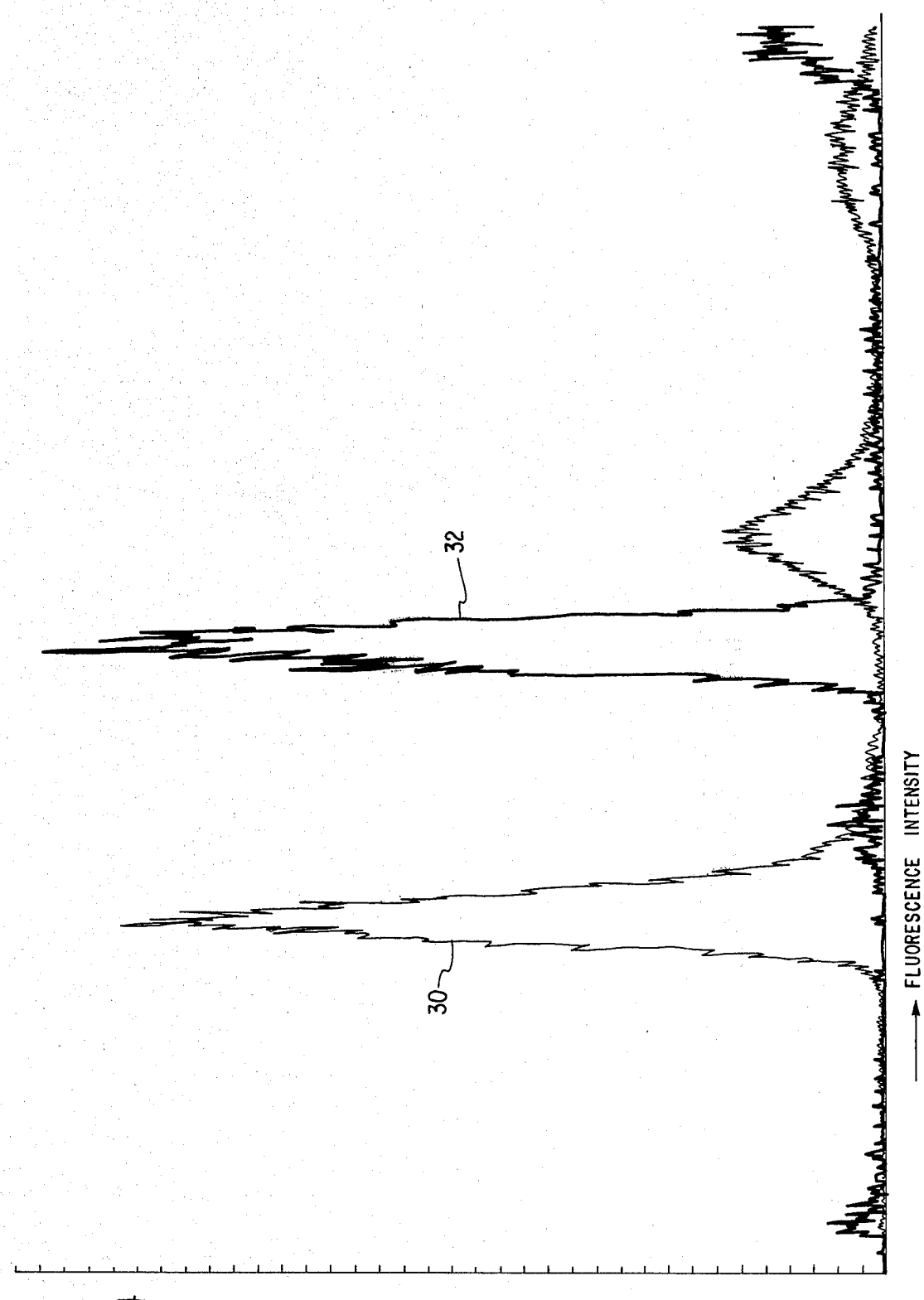
FIG. 4 is a histogram illustrating measurements obtained with apparatus according to the invention.

The results of one sequence of diffusion measurements carried out utilizing apparatus according to the invention is represented by the histogram of FIG. 4, where the ordinate N represents number of cell counts, and the abscissa represents fluorescence intensity. Biological cells 2 which have been fixed with alcohol and are carried in a solution 1 of alcohol and water are conducted through tube 3, while an aqueous solution 7 of the fluorescent dyes mithramycin and ethidium bromide, which bind to nucleus material (DNA) is conducted via tube 6. In the first part of the procedure, the selected dye concentration was not sufficiently high to enable the dye to reach all binding sites in the cell nucleus during the time of travel of the cells 2 from the outlet end of tube 3 to the axis of beam 17. The resulting fluorescence intensity distribution 30 exhibits a comparatively broad peak and low peak intensity. When the dye concentration in fluid 7 is increased, the dye substances will be attached to nearly all binding sites in the nucleus material during the available diffusion time. This resuts in the fluorescence intensity distribution 32, which presents a peak located at higher intensity values and having a smaller intensity variation.

In both procedures, the integral values of the fluorescence pulses generated by the cells as they pass the laser beam 17 are measured to produce the illustrated curves. Therefore, two cells that have been fused together during fixation, which is a common artifact due to fixation, yield twice the fluorescence intensity of a single cell. This leads to the second, smaller peak to the right of the maximum peak of each of the curves. Correspondingly, an aggregation of three cells gives rise to the next peak to the right, which is shown in FIG. 4 for curve 30, at an intensity level corresponding to three times that produced by a single cell.

By performing correlated size measurements, the higher fluorescence intensity readings can easily be identified as having been generated by cell aggregates.

Comparing the two histogram curves shown in FIG. 4, it can be noted that the main peak of curve 30 is asymmetrical and has a larger coefficient of variation than does the main peak of curve 32. The main peak of curve 30 is broadened to the right of its maximum value, which indicates that within the associated cell population there are a number of cells that have different membrane properties which allow dye to diffuse into the cell more rapidly.

With the apparatus according to the invention, it would be possible to obtain measurements for producing both curves at the same time by utilizing one of the double beam configurations shown in FIGS. 3. By varying the flow velocity and/or the distance between the axes of the laser beams, and/or different dye concentrations, any response having a main peak located at intensity levels below that of peak 32 can be derived, yielding information about membrane properties and/or diffusion coeffients within the cells.

It will be understood that the above description of the present invention is susceptible to various modifications, changes and adaptations, and the same are intended to be comprehended within the meaning and range of equivalents of the appended claims.

What is claimed is:

1. In apparatus for measuring reaction and/or diffusion of particles suspended in a fluid, which apparatus includes a supply tube for supplying a stream of the particle-containing fluid, a tapered tube surrounding the supply tube for providing a first entraining fluid stream and for encasing the particle-containing fluid in the first entraining fluid stream for the purpose of hydrodynamically focusing the particle-containing stream into a thin stream enclosed by the first fluid and in which the particles are separated from one another, means defining an outlet for passage of the thin stream and first fluid stream after leaving the tube, means producing a radiation beam which intersects the thin particle-containing stream, detector means disposed for detecting the radiation emanating from the separated particles, and a pulse evaluation circuit connected to the detector, the improvement comprising a further tube surrounding the supply tube and forming a further entraining fluid stream concentric with the particle-containing stream and the first entraining fluid stream, surrounding the particle-containing stream and flowing therewith through the tapered tube, said further entraining fluid stream having a composition selected to interact with the particles.

2. An arrangement as defined in claim 1 further comprising a jacket pipe extending between said tube and said outlet and enclosing the path of travel of the particle-containing fluid and the entraining streams.

3. An arrangement as defined in claim 1 or 2 wherein said further tube is mounted to be movable in the axial direction relative to said supply tube and both said further tube and said supply tube are movable in the axial direction relative to said tapered tube for permitting variation of the diameters of the further entraining fluid stream and of the particle-containing fluid stream.

4. An arrangement as defined in claim 1 wherein said detector means and said pulse evaluation circuit are arranged for producing, from the radiation emanating from the particles, a measurement of at least one of the extinction, fluorescence, radiation scattering and radiation diffraction produced by impingement of the radiation beam on the particles.

* * * * *